United States Patent
Dan et al.

(10) Patent No.: US 12,378,516 B2
(45) Date of Patent: *Aug. 5, 2025

(54) PASSAGE TIMING CALCULATION DEVICE, PASSAGE TIMING CALCULATION METHOD, AND RECORDING MEDIUM FOR RECORDING PROGRAM

(71) Applicants: NIKON CORPORATION, Tokyo (JP); KYOTO UNIVERSITY, Kyoto (JP)

(72) Inventors: Tomoro Dan, Yokohama (JP); Hiroaki Kii, Fujisawa (JP); Takayuki Uozumi, Machida (JP); Yoshiko Sato, Kyoto (JP); Shinsuke Yoshida, Kyoto (JP)

(73) Assignees: NIKON CORPORATION, Tokyo (JP); KYOTO UNIVERSITY, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/763,141

(22) Filed: Jul. 3, 2024

(65) Prior Publication Data

US 2024/0352397 A1    Oct. 24, 2024

Related U.S. Application Data

(63) Continuation of application No. 17/224,591, filed on Apr. 7, 2021, now Pat. No. 12,054,701, which is a continuation of application No. PCT/JP2019/038926, filed on Oct. 2, 2019.

(30) Foreign Application Priority Data

Oct. 12, 2018 (JP) .................................. 2018-193875

(51) Int. Cl.
*C12M 1/34* (2006.01)
*C12M 1/36* (2006.01)
(Continued)

(52) U.S. Cl.
CPC ............ *C12M 41/46* (2013.01); *C12M 41/36* (2013.01); *C12M 41/48* (2013.01); *C12N 5/0696* (2013.01); *C12M 31/10* (2013.01); *C12M 33/00* (2013.01)

(58) Field of Classification Search
CPC . C12M 4/46; C12M 4/36; C12M 4/48; C12M 33/00; C12N 5/0696
(Continued)

(56) References Cited

U.S. PATENT DOCUMENTS

| 11,155,782 B2 | 10/2021 | Okairi et al. |
| 12,054,701 B2 * | 8/2024 | Dan ..................... C12N 5/0696 |

(Continued)

FOREIGN PATENT DOCUMENTS

| WO | 2014/017480 A1 | 1/2014 |
| WO | 2016/013394 A1 | 1/2016 |

OTHER PUBLICATIONS

Dec. 24, 2019 International Search Report issued in International Patent Application No. PCT/JP2019/038926.
(Continued)

*Primary Examiner* — Gabriel I Garcia
(74) *Attorney, Agent, or Firm* — Oliff PLC

(57) ABSTRACT

A passage timing calculation device includes a processor and a memory encoded with instructions executed by the processor, wherein the instructions causing the processor to perform operations comprising calculating a time change in an area occupied by an extraction target region that is a region in which a striated pattern appears from a plurality of images of pluripotent stem cells captured at different times, detecting a change point of the time change in an area occupied by the extraction target region, and calculating a passage timing of the pluripotent stem cells on the basis of the change point.

15 Claims, 9 Drawing Sheets

(51) Int. Cl.
*C12N 5/074* (2010.01)
*C12M 1/00* (2006.01)
*C12M 1/26* (2006.01)

(58) Field of Classification Search
USPC .......................................................... 435/29
See application file for complete search history.

(56) References Cited

U.S. PATENT DOCUMENTS

| | | |
|---|---|---|
| 2009/0311781 A1 | 12/2009 | Amit et al. |
| 2012/0122143 A1* | 5/2012 | Mimura ................ G06T 7/0016 |
| | | 382/133 |
| 2017/0159003 A1 | 6/2017 | Shimase et al. |
| 2017/0199171 A1 | 7/2017 | Kiyota et al. |

OTHER PUBLICATIONS

Dec. 24, 2019 Written Opinion issued in International Patent Application No. PCT/JP2019/038926.
Jun. 30, 2022 Search Report issued in European Patent Application No. 19872004.7.
Dec. 11, 2023 Office Action issued in U.S. Appl. No. 17/224,591.
Dec. 11, 2023 Office Action issued Chinese Patent Application No. 201980066349.6.
Apr. 24, 2024 Notice of Allowance issued in U.S. Appl. No. 17/224,591.

* cited by examiner

PASSAGE TIMING CALCULATION DEVICE, PASSAGE TIMING CALCULATION METHOD, AND RECORDING MEDIUM FOR RECORDING PROGRAM

RELATED APPLICATIONS

This application is a continuation of U.S. patent application Ser. No. 17/224,591, filed Apr. 7, 2021, which is a continuation of International Application No. PCT/JP2019/038926, filed Oct. 2, 2019, which claims priority to Japanese Patent Application No. 2018-193875, filed Oct. 12, 2018. The entire contents of these prior applications are incorporated by reference herein.

TECHNICAL FIELD

The present invention relates to a passage timing calculation device, a passage timing calculation method, and a program.

BACKGROUND ART

A large amount of pluripotent stem cells is required in regenerative medicine. A process of increasing the number of cells in target cells is called an expansion culture process, but in an expansion culture of pluripotent stem cells such as artificial pluripotent stem cells (iPS cells), it is necessary to perform the expansion culture while maintaining pluripotency, that is, an undifferentiated state, of the pluripotent stem cells. For this reason, for cells that form colonies, such as iPS cells, the expansion culture is performed by subculturing the colonies. The pluripotent stem cells, which are iPS cells, change from an immature state to a mature state suitable for subculture in a culture process, and go through a colony state change in this process. In the expansion culture process, a timing for passage is determined on the basis of a change in colony state (referred to as "maturity of a colony" in this application). Conventionally, for the maturity, workers visually observe sizes of the cells in a colony to make a determination, but there may be variation among workers.

To suppress variation among workers regarding a timing of passage, a device that collects cells after the expansion culture to make a cell suspension, measures the number of cells per unit amount of the cell suspension, dilutes the cell suspension to a desired cell concentration on the basis of a result of the measurement, and automatically performs work of a subculture has been proposed (Patent Literature 1). However, since the device described in Patent Literature 1 causes cells to be peeled from a culture vessel, measures and adjusts the number of cells while collecting the cells in a collecting bag, and performs a subculture, it is not possible to determine whether maturity of a colony is sufficient, and if it is not sufficient, the culture cannot be continued to mature the colony. There is a need for a method with which the maturity of a colony that has been adherently cultured can be determined and the timing for a passage can be predicted.

CITATION LIST

Patent Literature

[Patent Literature 1]
PCT International Publication No. WO2016/013394

SUMMARY OF INVENTION

Solution to Problem

To solve the problems described above, according to one aspect of the present invention, there is a passage timing calculation device that includes a processor and a memory encoded with instructions executed by the processor, wherein the instructions causing the processor to perform operations comprising calculating a time change in an area occupied by an extraction target region that is a region in which a striated pattern appears from a plurality of images of pluripotent stem cells captured at different times, detecting a change point of the time change in an area occupied by the extraction target region, and calculating a passage timing of the pluripotent stem cells on the basis of the change point.

To solve the problems described above, according to another aspect of the present invention, there is a passage timing calculation method that includes a time change calculation process that calculates a time change in an area occupied by an extraction target region that is a region in which a striated pattern appears from a plurality of microscope images of pluripotent stem cells captured at different times, a change point detection process that detects a change point of the time change in an area occupied by the extraction target region; and a passage timing calculation process that calculates a passage timing of the pluripotent stem cells on the basis of the change point.

To solve the problems described above, according to still another aspect of the present invention, there is a recording medium for recording a program for causing a computer to execute a time change calculation step of calculating a time change in an area occupied by an extraction target region that is a region in which a striated pattern appears from a plurality of microscope images of pluripotent stem cells captured at different times, a change point detection step of detecting a change point of the time change in an area occupied by the extraction target region; and a passage timing calculation step of calculating a passage timing of the pluripotent stem cells on the basis of the change point.

DESCRIPTION OF EMBODIMENTS

First Embodiment

Figure 1:
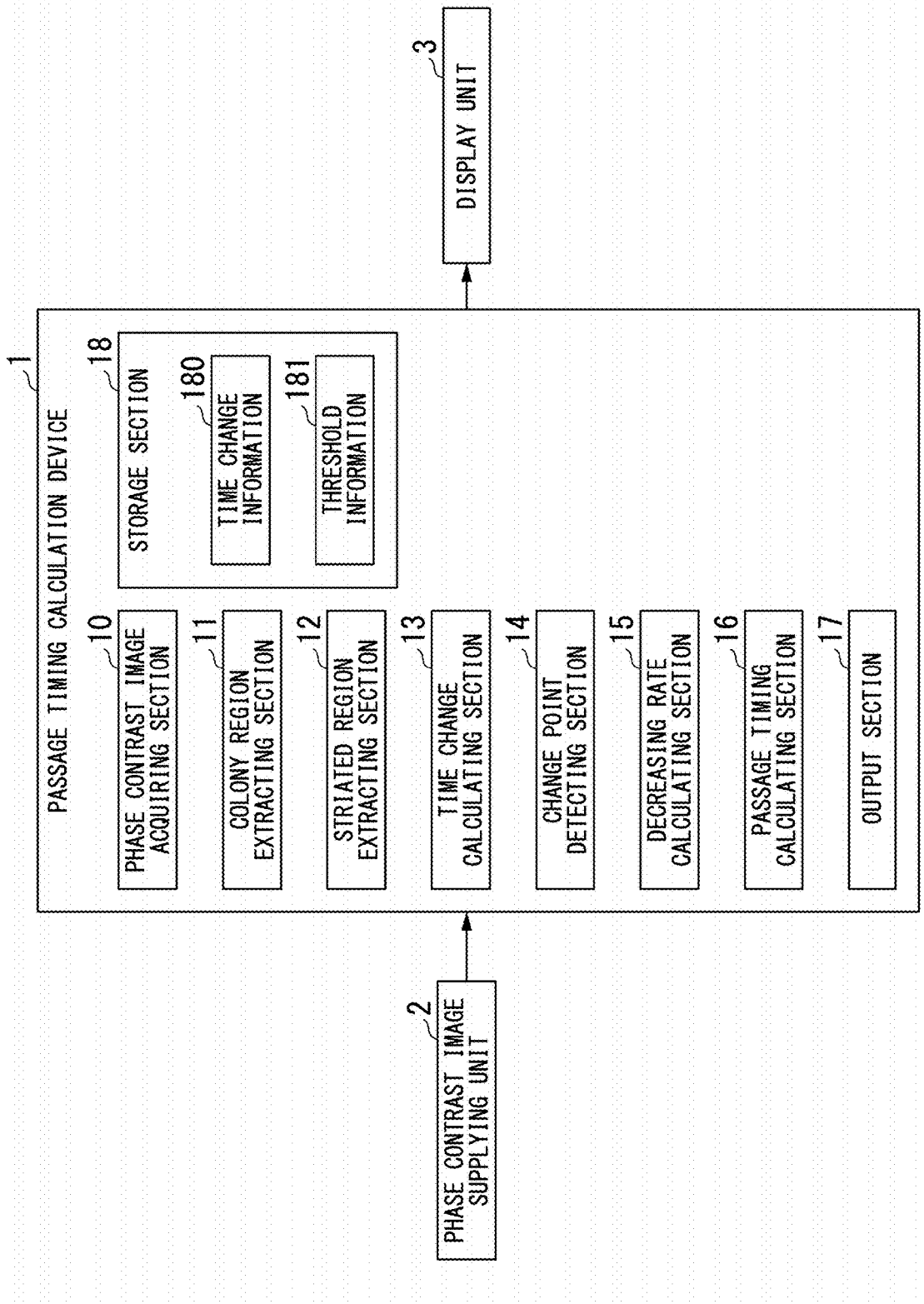
FIG. 1 is a diagram which shows an example of a configuration of a passage timing calculation device according to a first embodiment of the present invention.

Hereinafter, embodiments of the present invention will be described with reference to the drawings. FIG. 1 is a diagram which shows an example of a configuration of a passage timing calculation device 1 according to the present embodiment. The passage timing calculation device 1 extracts an extraction target region, which is a region to be extracted, from a plurality of phase contrast images PS (not shown) in which pluripotent stem cells are imaged. Here, pluripotent stem cells are stem cells that have a potential capability (pluripotency) to differentiate into all cell types belonging to three germ layers of endoderm, mesodermal, and ectoderm and are also proliferative, and iPS cells and embryonic stem cells (ES cells) are examples.

Figure 2:
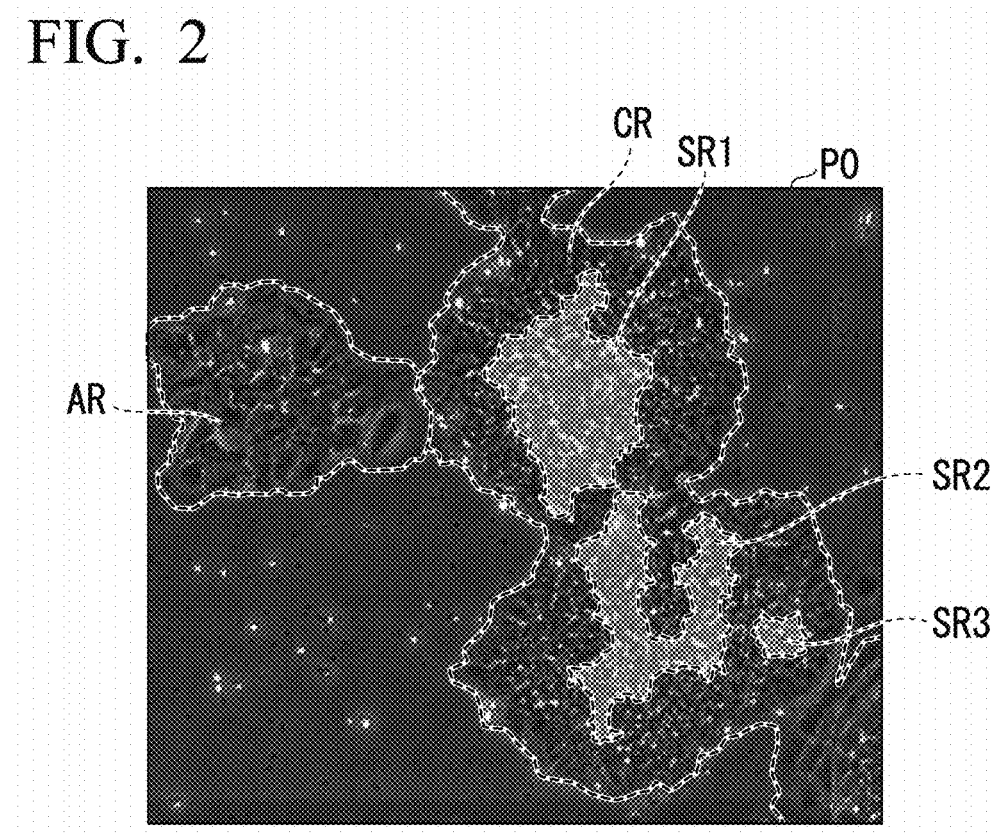
FIG. 2 is a diagram which shows an example of a phase contrast image according to the first embodiment of the present invention.

The plurality of phase contrast images PS are a set of timelapse images of the colonies of pluripotent stem cells captured at a predetermined time interval, and one image of the phase contrast images PS is referred to as a phase contrast image P0. An example of the phase contrast image P0 is shown in FIG. 2.

The extract target region in this embodiment is a region in which a striated pattern appears in the phase contrast image P0. Here, a culture process of pluripotent stem cells, which are iPS cells, will be described to describe the striated pattern.

The pluripotent stem cells, which are iPS cells, change from a colony-unformed state set as an initial state to a mature state through an immature state in the culture process.

The colony-unformed state is a state in which the pluripotent stem cells are single cells and do not form a colony. In the colony immature state, a colony is formed, but an area per cell is large and a cell density is low. Hereinafter, a region having a low cell density is also referred to as a coarse region.

The mature state is a state in which pluripotent stem cells form colonies and become mature. As the pluripotent stem cells mature, the area per cell in the colony becomes smaller and the cell density increases. Hereinafter, a region having a high cell density is also referred to as a dense region. In a colony in the mature state, a dense region is formed in the center, and a coarse region surrounds the dense region.

There is a transition state as an intermediate state between the colony immature state and the mature state. The transition state is a state in which the pluripotent stem cells form colonies but are not sufficiently mature.

Figure 11:
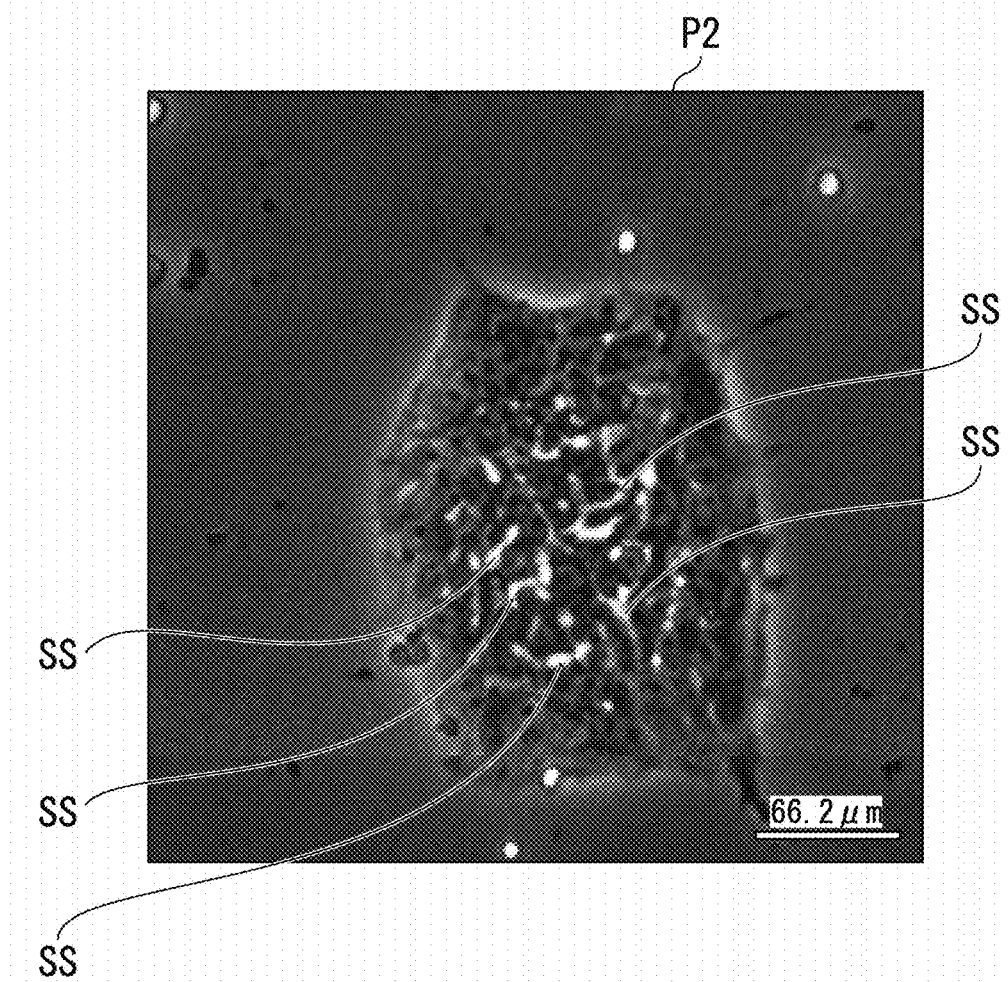
FIG. 11 is a diagram which shows an example of a striated pattern according to the first embodiment of the present invention.

In the transition state, a striated region can be seen in the phase contrast image P0 of a colony. The striated region is a region in which a plurality of elongated striated patterns can be seen in the phase contrast image P0. As the pluripotent stem cells mature, the pluripotent stem cells become denser, and as a result, it is considered that a contrast in gap between the plurality of pluripotent stem cells becomes higher, and appears striated. FIG. 11 shows an example of a striated pattern SS.

In the transition state, a colony includes a striated region, a dense region that surrounds the striated region, and a coarse region that surrounds the dense region.

Here, a striated region SR will be described with reference to FIG. 2.

FIG. 2 is a diagram which shows an example of the phase contrast image P0 obtained by capturing images of iPS cells (iPS cell line 003 derived from healthy human peripheral blood, generated by the Center for iPS Cell Research and Application, Kyoto University) according to the present embodiment. In FIG. 2, as examples of the striated region SR included in a colony region CR of the phase contrast image P0, a striated region SR1, a striated region SR2, and a striated region SR3 are shown.

The colony region CR is a region excluding an abnormal region AR among regions corresponding to the colonies of pluripotent stem cells in the phase contrast image P0.

The abnormal region AR is a region formed by abnormal cells that deviate from a state of pluripotent stem cells among the regions corresponding to the colonies of the pluripotent stem cells. In culturing the pluripotent stem cells, it is important to maintain a pluripotent state, but abnormal cells that deviate from the state of the pluripotent stem cells may appear in a process of culturing.

Returning to FIG. 1, the description of the passage timing calculation device 1 will be continued.

The passage timing calculation device 1 includes a phase contrast image acquiring section 10, a colony region extracting section 11, a striated region extracting section 12, a time change calculating section 13, a change point detecting section 14, a decreasing rate calculating section 15, a passage timing calculating section 16, an output section 17, and a storage section 18.

The phase contrast image acquiring section 10 acquires a plurality of phase contrast images PS supplied from a phase contrast image supplying unit 2. Here, the plurality of phase contrast images PS are an example of a plurality of microscope images in which the pluripotent stem cells are imaged by transmitted illumination at different times. The plurality of phase contrast images PS are timelapse images in which the pluripotent stem cells are imaged at different times by converting a phase difference of transmitted light of an illumination light applied to the pluripotent stem cells into a light-dark difference. In the plurality of phase contrast image PS, for example, magnified images of the pluripotent stem cells obtained by a phase contrast microscope are captured.

The plurality of phase contrast images PS are a plurality of images in which the pluripotent stem cells are imaged at a fixed time interval.

The microscope images by transmitted illumination may be, for example, differential interference images, quantitative phase images, or the like, in addition to the phase contrast images.

The colony region extracting section 11 extracts a colony region CR of the pluripotent stem cells from each phase contrast image P0.

The striated region extracting section 12 extracts the striated region SR from the colony region CR in each phase contrast image P0. The striated region SR is an example of the extraction target region, and is a region in which the striated pattern appears in the phase contrast image P0.

Here, the striated region extracting section 12 can extract, for example, the striated region SR on the basis of a striated high-luminance region. The high-luminance region is a region based on a group of pixels having a luminance value larger than a reference value among pixels constituting the phase contrast image P0. The high-luminance region includes the group of pixels having a luminance value larger than the reference value and a periphery of the group of pixels.

The time change calculating section 13 calculates a time change G1 in an area occupied by the striated region SR in the plurality of phase contrast images PS. In the present embodiment, the time change calculating section 13 first calculates a striated region ratio A in each phase contrast image P0. Here, the striated region ratio A is a ratio of the area occupied by the striated region SR to the colony region CR.

The time change calculating section 13 causes the time change G1 of the striated region ratio A in the plurality of phase contrast images PS to be stored in the storage section 18 as time change information 180 on the basis of a time at which each phase contrast image P0 is captured and the striated region ratio A of the time.

The change point detecting section 14 detects a change point M1 of the time change G1 calculated by the time change calculating section 13. Here, the change point M1 is a point indicating a time at which a ratio of an area of the striated region SR to an entire area of the colony region CR starts to decrease after having increased once. The change point M1 is, for example, a point at which a slope of the time change G1 changes from positive to negative. That is, the change point M1 is a maximum value of the time change G1.

The present inventors have found that, if the colonies of the pluripotent stem cells are cultured from an immature state to a mature state, the ratio of the area of the striated region SR to the entire area of the colony region CR (the striated region ratio A) decreases after having increased once, and eventually, the striated region SR is almost eliminated. Therefore, it is possible to determine a maturity on the basis of a change in the striated region ratio A.

The decreasing rate calculating section 15 calculates a decreasing rate D of the area occupied by the striated region SR to the colony region CR after the change point M1 detected by the change point detecting section 14 for the time change G1 calculated by the time change calculating section 13.

In the present embodiment, the decreasing rate calculating section 15 calculates the decreasing rate D of the striated region ratio A after the change point M1 for the time change G1. Here, the decreasing rate D is, for example, the decreasing amount of the striated region ratio A per hour.

The passage timing calculating section 16 calculates a passage timing PT of the pluripotent stem cells on the basis of the change point M1.

In the present embodiment, the passage timing calculating section 16 calculates the passage timing PT of the pluripotent stem cells on the basis of the decreasing rate D and a predetermined threshold value TH. In the present embodiment, the passage timing calculating section 16 calculates a period of time in which the striated region ratio A is equal to or less than the threshold value TH indicated by the threshold information 181 from the decreasing rate D as the passage timing PT. Here, the threshold information 181 is information indicating a predetermined threshold value of the striated region ratio A.

The output section 17 outputs the passage timing PT to the display unit 3 and causes the display unit 3 to display the passage timing PT. Note that the output section 17 may output the passage timing PT to an output device other than the display unit 3, a storage device, or the like.

The time change information 180 and the threshold information 181 are stored in the storage section 18.

The phase contrast image supplying unit 2 supplies a plurality of phase contrast images P0 to the passage timing calculation device 1. The phase contrast image supplying unit 2 is, for example, an imaging device including a phase contrast microscope.

The display unit 3 displays the passage timing PT supplied from the passage timing calculation device 1. The display unit 3 is, for example, a display device such as a display.

Next, processing in which the passage timing calculation device 1 calculates the passage timing PT will be described with reference to FIGS. 3 to 5.

Figure 3:
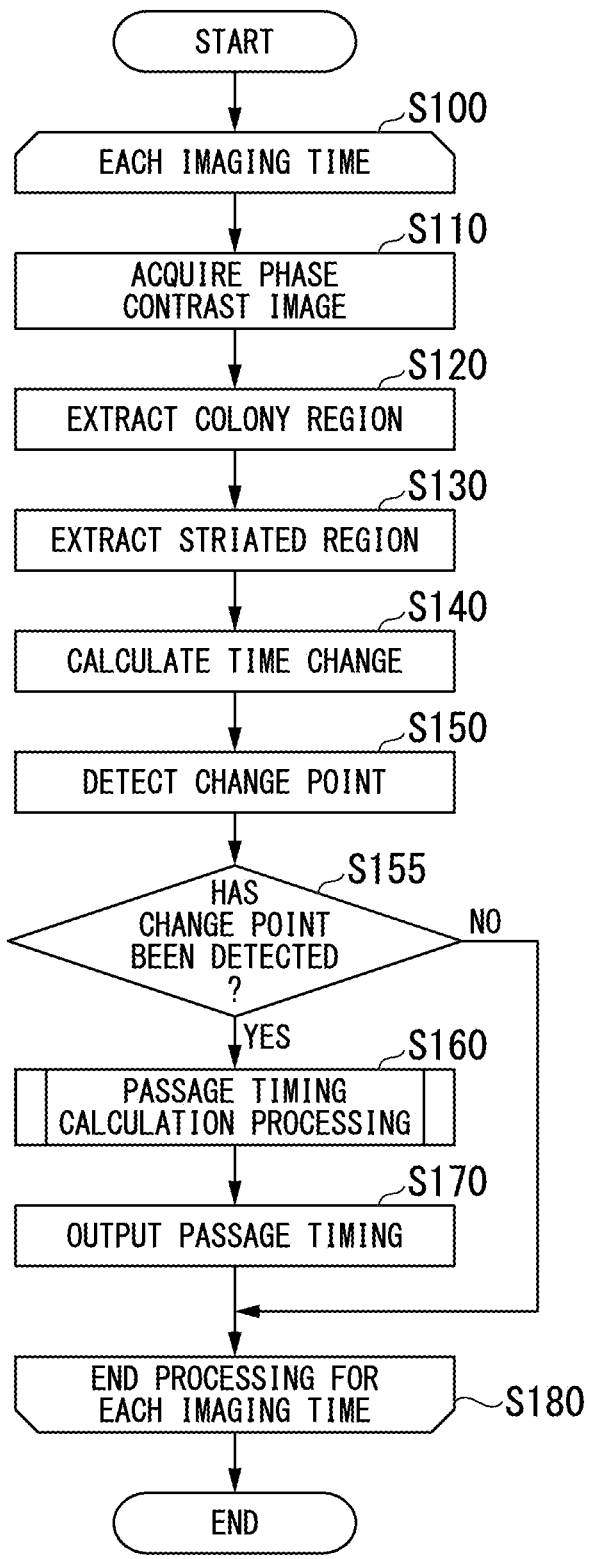
FIG. 3 is a diagram which shows an example of processing of the passage timing calculation device according to the first embodiment of the present invention.

FIG. 3 is a diagram which shows an example of processing of the passage timing calculation device 1 according to the present embodiment.

Step S100: The passage timing calculation device 1 starts processing of calculating the passage timing PT for each imaging time of the plurality of phase contrast images PS. Here, in the present embodiment, the number of frames N of the plurality of phase contrast images PS is predetermined. The passage timing calculation device 1 repeats the processing of calculating the passage timing PT by the predetermined number of frames N.

Step S110: The phase contrast image acquiring section 10 acquires the phase contrast image P0 supplied from the phase contrast image supplying unit 2. Here, the phase contrast image supplying unit 2 supplies the captured phase contrast image P0 to the passage timing calculation device 1 each time the phase contrast image P0 is captured.

The phase contrast image acquiring section 10 supplies the acquired phase contrast image P0 to the colony region extracting section 11 and the striated region extracting section 12.

Step S120: The colony region extracting section 11 extracts the colony region CR of the pluripotent stem cells from the phase contrast image P0 acquired by the phase contrast image acquiring section 10. The colony region extracting section 11 extracts, for example, the cell region from the phase contrast image P0 on the basis of known edge detection, and extracts a cell region wider than a predetermined area as the colony region CR from the extracted cell region. The colony region extracting section 11 supplies the extracted colony region CR to the striated region extracting section 12 and the time change calculating section 13.

Note that the extraction of the colony region CR is not limited to a method performed on the basis of the area of a cell region, and can be performed by various known methods.

Here, the colony region extracting section 11 may extract a region excluding an abnormal region AR as the colony region CR on the basis of the presence or absence of surrounding halos.

A halo is a portion of a phase contrast image in which a phase contrast between one region and another region is large, and as a result, a brightness is higher than the surroundings at a boundary between the one region and the other region. The colonies of normal pluripotent stem cells have many halos around them, and the colonies of abnormal cells have few halos around them.

Therefore, the colony region CR can be set as a region which has a portion whose phase difference is equal to or greater than a predetermined value in the surroundings among regions in which colonies are formed. The abnormal region AR can be a region which does not have the portion whose phase difference is equal to or greater than the predetermined value in the surroundings in the colony region CR.

Step S130: The striated region extracting section 12 extracts the striated region SR from the colony region CR in the phase contrast image P0. Here, the striated region extracting section 12 can extract the striated region SR on the basis of a striated high-luminance region. The striated region extracting section 12 supplies the extracted striated region SR to the time change calculating section 13.

Step S140: The time change calculating section 13 calculates the time change G1 of the ratio (the striated region ratio A) of the area occupied by the striated region SR to the colony region CR.

The time change calculating section 13 first calculates the striated region ratio A for each phase contrast image P0. Here, for convenience, among the plurality of phase contrast images PS, the phase contrast image P0 acquired this time is set as a phase contrast image $P_n$, and phase contrast images acquired so far are set as phase contrast images $P_0$ to $P_{n-1}$. The time change calculating section 13 acquires the time change information 180 calculated on the basis of the phase contrast images $P_0$ to $P_{n-1}$ from the storage section 18, and calculates the time change G1 based on the phase contrast images $P_0$ to $P_n$ by adding a set of an imaging time of the phase contrast image $P_n$ and the calculated area ratio to the time change G1 indicated by the acquired time change information 180.

The time change calculating section 13 causes the storage section 18 to store the time change G1 calculated on the basis of the phase contrast images $P_0$ to $P_n$ as the time change information 180. Moreover, the time change calculating section 13 supplies the calculated time change G1 to the change point detecting section 14.

As described above, the time change calculating section 13 calculates the time change G1 of the striated region ratio A from the plurality of phase contrast images PS.

Step S150: The change point detecting section 14 detects the change point M1 of the time change G1.

Here, the time change G1 will be described with reference to FIG. 4.

Figure 4:
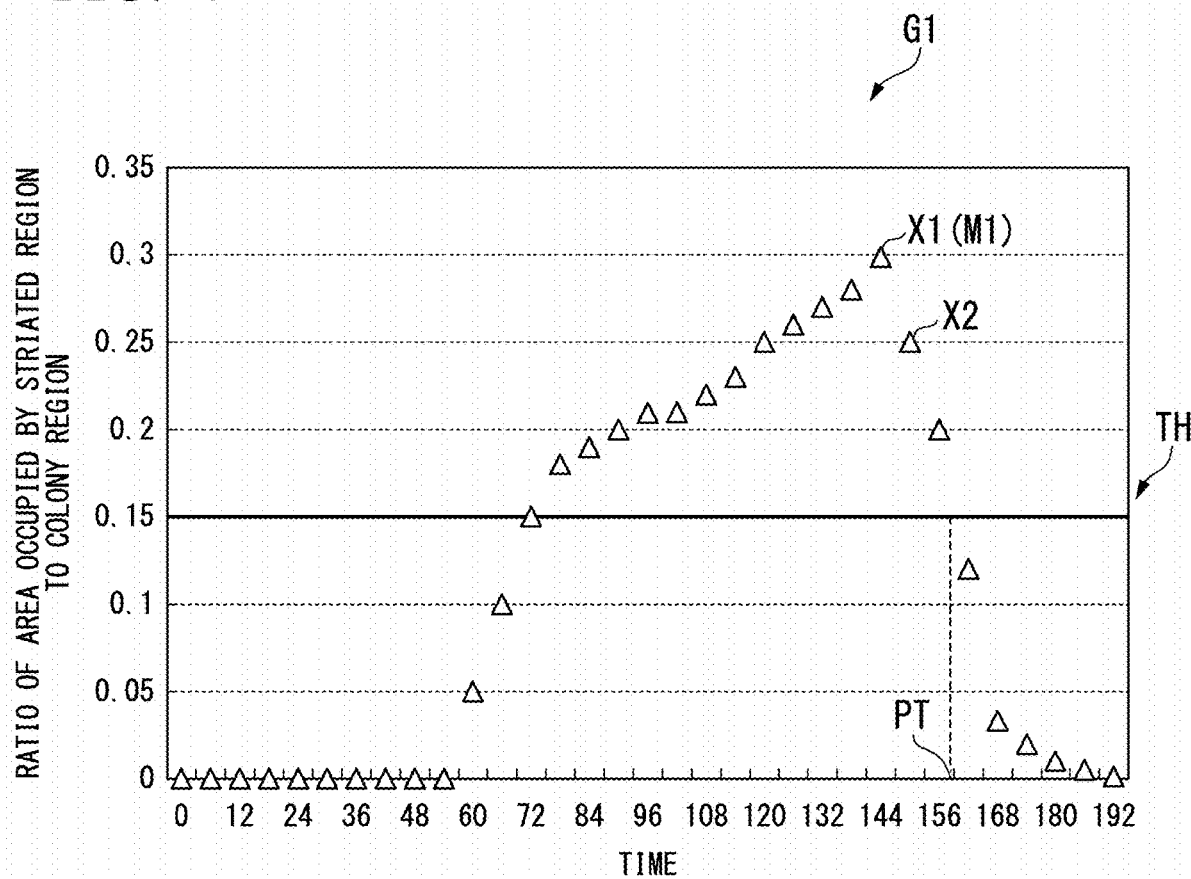
FIG. 4 is a diagram which shows an example of a time change of a ratio of an area occupied by a striated region to a colony region (a striated region ratio) according to the first embodiment of the present invention.

FIG. 4 is a diagram which shows an example of the time change G1 of the ratio (the striated region ratio A) of the area occupied by the striated region SR to the colony region CR according to the present embodiment. In the time change G1, the striated region ratio A is shown for each time at which the phase contrast image P0 is captured.

Note that the example of the time change G1 shown in FIG. 4 is virtual data that imitates the time change G1 of the striated region ratio A.

In the time change G1 shown in FIG. 4, the striated region ratio A increases to a point X1 and starts decreasing from the point X1. The change point detecting section 14 compares the striated region ratios A at adjacent points, and when it is determined that the striated region ratio A increases to the point X1, and the striated region ratio A is decreasing for the first time from the point X1 to a point X2, detects the point X1 as the change point M1.

In addition, the change point detecting section 14 may detect the change point M1 of the time change G1 as a point at which the slope of the time change G1 changes from positive to negative. As described above, in the present embodiment, the change point M1 can be easily detected.

Moreover, when the striated region ratio A is decreasing at three or more consecutive points of the time change G1, the change point detecting section 14 may detect any one of the three or more consecutive points (for example, the most recent point of an imaging time) as the change point M1. Here, the fact that a plurality of points are consecutive in the time change G1 means that there is no imaging time corresponding to a point other than the plurality of points between imaging times corresponding to the plurality of points. That is, times at which a plurality of phase contrast images PS are captured are consecutive frames.

For example, for the consecutive points X1, X2, and X3 in the time change G1, when the striated region ratio A at the point X2 is decreasing from the striated region ratio A at the point X1, and the striated region ratio A at the point X3 is decreasing from the striated region ratio A at the point X2, the change point detecting section 14 may detect the point X1 as the change point M1.

The passage timing calculation device 1 can improve the accuracy in the detection of the change point M1 when it is determined that the striated region ratio A is decreasing on the basis of three consecutive points as compared with a case in which it is determined on the basis of two consecutive points.

Moreover, when the slope of the time change G1 is smaller than a predetermined negative value, the change point detecting section 14 may also detect a point corresponding to the earliest imaging time among points in the time change G1 used to calculate a slope as the change point M1.

Note that the two or more points in the time change G1 used for the detection of the change point M1 by the change point detecting section 14 do not have to be consecutive.

Returning to FIG. 3, description of the processing performed by the passage timing calculation device 1 will be continued.

Step S155: The change point detecting section 14 determines whether the change point M1 has been detected. The change point detecting section 14 determines that the change point M1 has been detected when the change point M1 is detected in step S150, and determines that the change point M1 has not been detected when the change point M1 is not detected in step S150.

When it is determined that the change point M1 has been detected (YES in step S155), the change point detecting section 14 supplies the change point information indicating the detected change point M1 to the decreasing rate calculating section 15. Thereafter, the passage timing calculation device 1 executes processing of step S160.

On the other hand, when the change point detecting section 14 determines that the change point M1 has not been detected (NO in step S155), the passage timing calculation device 1 executes processing of step S180.

Step S160: The passage timing calculating section 16 and the decreasing rate calculating section 15 perform passage timing calculation processing.

Here, the passage timing calculation processing will be described with reference to FIG. 5.

Figure 5:
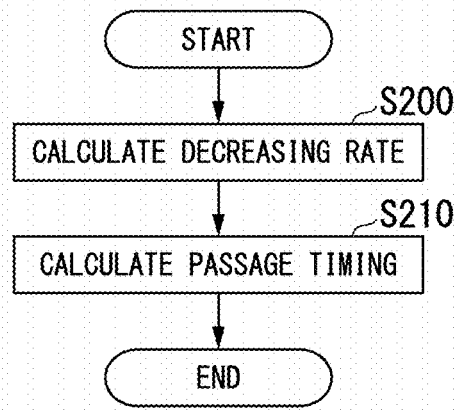
FIG. 5 is a diagram which shows an example of subculture passage timing processing according to the first embodiment of the present invention.

FIG. 5 is a diagram which shows an example of the passage timing calculation processing according to the present embodiment.

Step S200: The decreasing rate calculating section 15 calculates the decreasing rate D of the striated region ratio A after the change point M1 for the time change G1. Here, a term after the change point M1 refers to a range of an imaging time after an imaging time of the phase contrast image P0 corresponding to the change point M1.

The decreasing rate calculating section 15 supplies the calculated decreasing rate D to the passage timing stage calculating section 16.

Here, the processing in which the decreasing rate calculating section 15 calculates a decreasing rate will be described with reference to FIG. 4 again.

As an example, the decreasing rate calculating section 15 calculates a decreasing rate of the striated region ratio A by dividing a difference between the striated region ratio A corresponding to the point X2 and the striated region ratio A corresponding to the point X1 by a difference between an imaging time of the phase contrast image P0 corresponding to the point X2 and an imaging time of the phase contrast image P0 corresponding to the point X1. That is, in the present embodiment, the decreasing rate D is a value of a slope of a straight line connecting the points X1 and X2.

The decreasing rate calculating section 15 may calculate the decreasing rate D of the striated region ratio A on the basis of a plurality of points after the change point M1 in the time change G1. The plurality of points after the change point M1 are one or more points after the point X2 in addition to the point X1 and the point X2.

Returning to FIG. 5, description of the passage timing calculation processing will be continued.

Step S210: The passage timing calculating section 16 calculates the passage timing PT of the pluripotent stem cells on the basis of the decreasing rate D calculated by the decreasing rate calculating section 15 and the threshold value TH indicated by the threshold information 181 obtained from the storage section 18.

Here, when a passage timing PT calculated in the second and subsequent processings of step S210 is different from a passage timing PT calculated in the previous processing of step S210, the passage timing calculating section 16 corrects the passage timing PT according to the newly calculated passage timing PT. The passage timing calculating section 16 calculates the corrected passage timing PT as the passage timing PT.

The passage timing calculating section 16 supplies the calculated passage timing PT to the output section 17.

In the passage timing calculation device 1, since the processing of calculating the passage timing PT is continuously repeated by the number N of frames of the plurality of phase contrast images PS, the passage timing PT calculated once can be corrected, and thus the accuracy of the passage timing PT can be improved.

Here, processing in which the passage timing calculating section 16 calculates the passage timing PT will be described with reference to FIG. 4 again.

The passage timing calculating section 16 calculates a time at which the striated region ratio A is equal to or less than the threshold value TH on the basis of the decreasing rate D. Here, the threshold value TH is 15% as an example. The passage timing calculating section 16 sets the calculated time as the passage timing PT.

As described above, since the decreasing rate D is a value of the slope of the straight line connecting the points X1 and X2, the passage timing calculating section 16 calculates the passage timing PT on the basis of the approximation according to a linear equation of the time change G1 after the change point M1 as an example in the present embodiment.

Note that the passage timing calculating section 16 may calculate an approximation curve that approximates a range after the change point M1 of the time change G1 by using a plurality of points after the change point M1 in the time change G1. The passage timing calculating section 16 may calculate the imaging time of the phase contrast image P0 at which the striated region ratio A is equal to or less than the threshold value TH on the basis of the calculated approximation curve.

Returning to FIG. 3, the description of the processing performed by the passage timing calculation device 1 will be continued.

Step S170: The output section 17 outputs the passage timing PT calculated by the passage timing calculating section 16 to the display unit 3, and causes the display unit 3 to display the passage timing PT.

Step S180: When the passage timing calculation device 1 has executed the processing of calculating the passage timing PT for each imaging time of the plurality of phase contrast images PS by the number of frames N, it ends the processing.

In the present embodiment, the case in which the phase contrast image supplying unit 2 supplies a captured phase contrast image P0 to the passage timing calculation device 1 each time the phase contrast image P0 is captured has been described, but the present invention is not limited thereto. The phase contrast image supplying unit 2 may also supply a plurality of captured phase contrast images P0s collectively to the passage timing calculation device 1 at a predetermined timing.

As described above, the passage timing calculation device 1 according to the present embodiment includes a time change calculating section 13, a change point detecting section 14, and a passage timing calculating section 16.

The time change calculating section 13 calculates the time change G1 of the area (the striated region ratio A in this example) occupied by an extraction target region (the striated region SR in this example) that is a region in which the striated pattern appears from a plurality of microscope images (the plurality of phase contrast images PS in this example) in which pluripotent stem cells are imaged by transmitted illumination at different times.

With this configuration, the passage timing calculation device 1 according to the present embodiment can predict the timing for a passage, so that it is possible to perform a passage at an appropriate timing. The present inventors have found that when the colonies of the pluripotent stem cells become over-mature after the maturation state, the survival and proliferation after a passage are poor. However, according to the passage timing calculation device 1 according to the present embodiment, it is possible to predict an optimum passage timing by setting an appropriate threshold value TH and to reduce a risk of pluripotent stem cells in culture becoming over-mature.

In addition, the passage timing calculation device 1 according to the present embodiment includes a decreasing rate calculating section 15.

The decreasing rate calculating section 15 calculates the decreasing rate D of an area after the change point M1 (the striated region ratio A in this example) for the time change G1.

The passage timing calculating section 16 calculates the passage timing PT on the basis of the decreasing rate D and the predetermined threshold value TH.

With this configuration, since the passage timing calculation device 1 according to the present embodiment can calculate the decreasing rate D of the striated region ratio A and calculate the passage timing PT on the basis of the calculated decreasing rate D, it is possible to improve the accuracy in the calculation of the passage timing PT as compared with a case in which the decreasing rate D is not calculated.

Second Embodiment

A second embodiment of the present invention will be described in detail with reference to the drawings.

In the first embodiment described above, the case in which the passage timing calculation device calculates a passage timing on the basis of the decreasing rate of the striated region ratio A and the predetermined threshold value has been described. In the present embodiment, a case in which the passage timing calculation device calculates a passage timing on the basis of passage timing information in which a change point and a passage timing are associated with each type of pluripotent stem cells in advance will be described.

The passage timing calculation device according to the present embodiment is referred to as a passage timing calculation device 1a.

Figure 6:
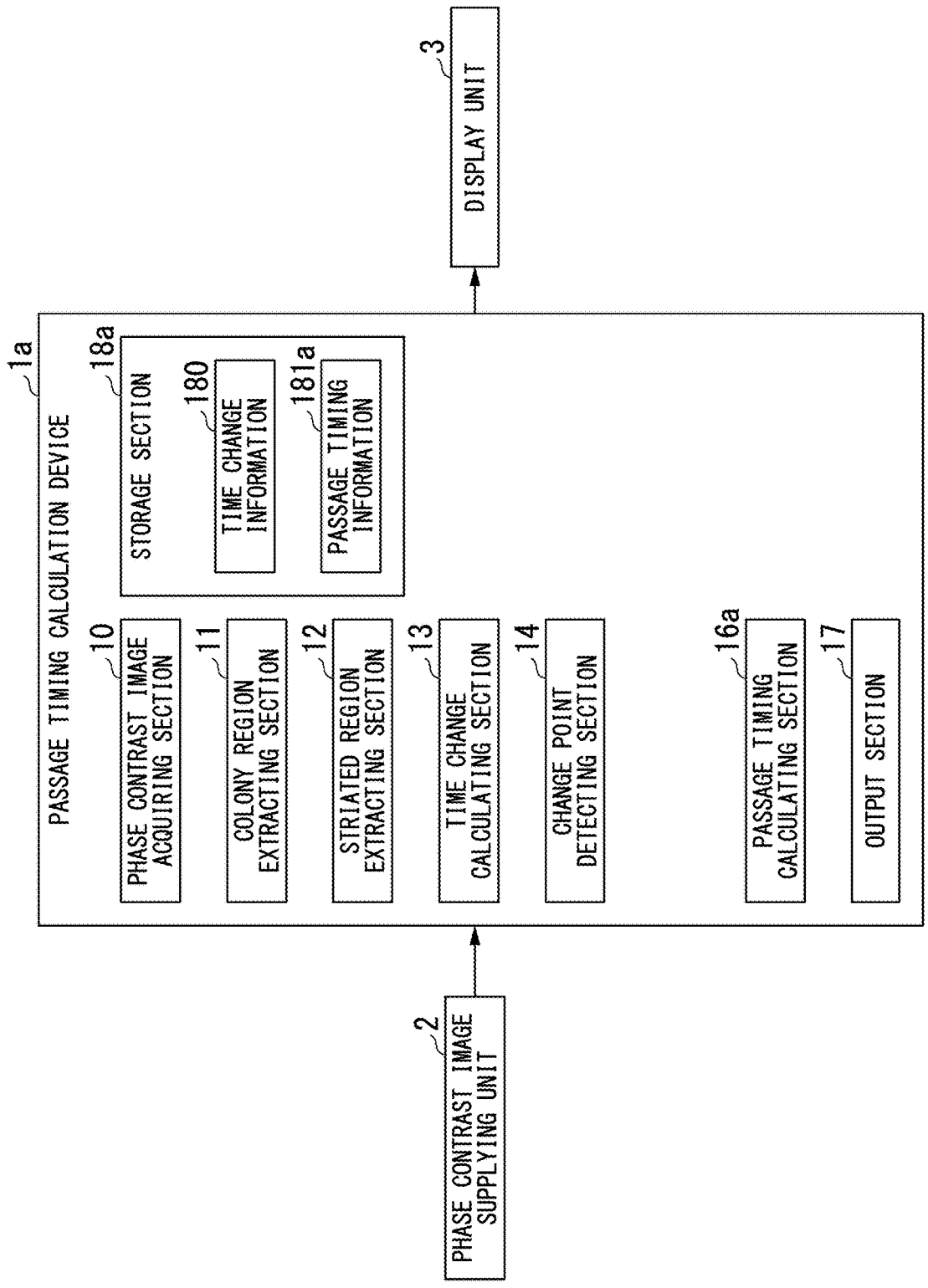
FIG. 6 is a diagram which shows an example of a configuration of a passage timing calculation device according to a second embodiment of the present invention.

FIG. 6 is a diagram which shows an example of the configuration of the passage timing calculation device 1a according to the present embodiment. If the passage timing calculation device 1a (FIG. 6) according to the present embodiment is compared with the passage timing calculation device 1 (FIG. 2) according to the first embodiment, these are different in the passage timing calculating section 16a and the storage section 18a. Here, functions of other components (the phase contrast image acquiring section 10, the colony region extracting section 11, the striated region extracting section 12, the time change calculating section 13, the change point detecting section 14, the decreasing rate calculating section 15, and the output section 17) are the same as those in the first embodiment. The description of the same function as that of the first embodiment will be omitted, and a portion different from the first embodiment will be mainly described in the second embodiment.

The passage timing calculating section 16a calculates the passage timing PT on the basis of the change point M1 and the passage timing information 181a. The passage timing information 181a is information in which the change point M1 and the passage timing PT are associated with each type of pluripotent stem cells in advance.

The storage section 18 stores time change information 180 and passage timing information 181a.

Here, in the passage timing information 181a, for example, the change point M1 and the passage timing PT are calculated in advance for each type of pluripotent stem cells and stored in the storage section 18 on the basis of the processing (FIG. 3) in which the passage timing calculation device 1 described in the first embodiment performs a passage timing calculation.

Next, with reference to FIG. 7, the processing in which the passage timing calculation device 1a calculates the passage timing PT will be described. The processing in which the passage timing calculation device 1a calculates the passage timing PT and the processing in which the passage timing calculation device 1 of the first embodiment calculates a passage timing (FIG. 3) are different from each other in the passage timing calculation processing of step S160.

Figure 7:
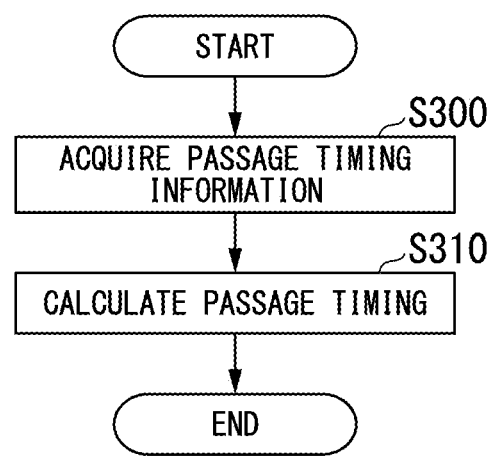
FIG. 7 is a diagram which shows an example of passage timing calculation processing according to the second embodiment of the present invention.

FIG. 7 is a diagram which shows an example of the passage timing calculation processing according to the present embodiment.

Step S300: The passage timing calculating section 16a acquires the passage timing information 181a from the storage section 18a.

Step S310: The passage timing calculating section 16a calculates the passage timing PT on the basis of the change point M1 and the passage timing information 181a. Here, the passage timing calculating section 16a selects information corresponding to a type of pluripotent stem cells from the passage timing information 181a, and reads the passage timing PT corresponding to the change point M1 from the selected information to calculate the passage timing PT.

As described above, in the passage timing calculation device 1a according to the present embodiment, the passage timing calculating section 16a calculates the passage timing PT on the basis of the change point M1 detected by the change point detecting section 14 and the passage timing information 181a in which the change point M1 and the passage timing PT are associated with each type of pluripotent stem cells in advance.

With this configuration, in the passage timing calculation device 1a according to the present embodiment, since the passage timing PT can be calculated on the basis of the passage timing information 181a in which the change point M1 and the passage timing PT are associated with each type of pluripotent stem cells in advance, a processing load can be reduced as compared with a case in which the calculation is not based on the passage timing information 181a.

In the present embodiment, the passage timing information 181a is assumed to be information in which the change point M1 and the passage timing PT are associated with each type of pluripotent stem cells in advance, but the passage timing information 181a may also be information in which the change point M1 and the passage timing PT are associated with the type and the number of pluripotent stem cells in advance.

Third Embodiment

Hereinafter, a third embodiment of the present invention will be described in detail with reference to the drawings.

In the first embodiment and the second embodiment described above, a case in which the passage timing calculation device continuously repeats the processing of calculating a passage timing by the number of frames of a plurality of phase contrast images has been described. In the present embodiment, a case in which the passage timing calculation device cancels the processing when a passage timing is calculated will be described. Moreover, a case in which the passage timing calculation device changes a time interval at which pluripotent stem cells are imaged will be described in the present embodiment.

The passage timing calculation device according to the present embodiment is referred to as a passage timing calculation device 1b.

Figure 8:
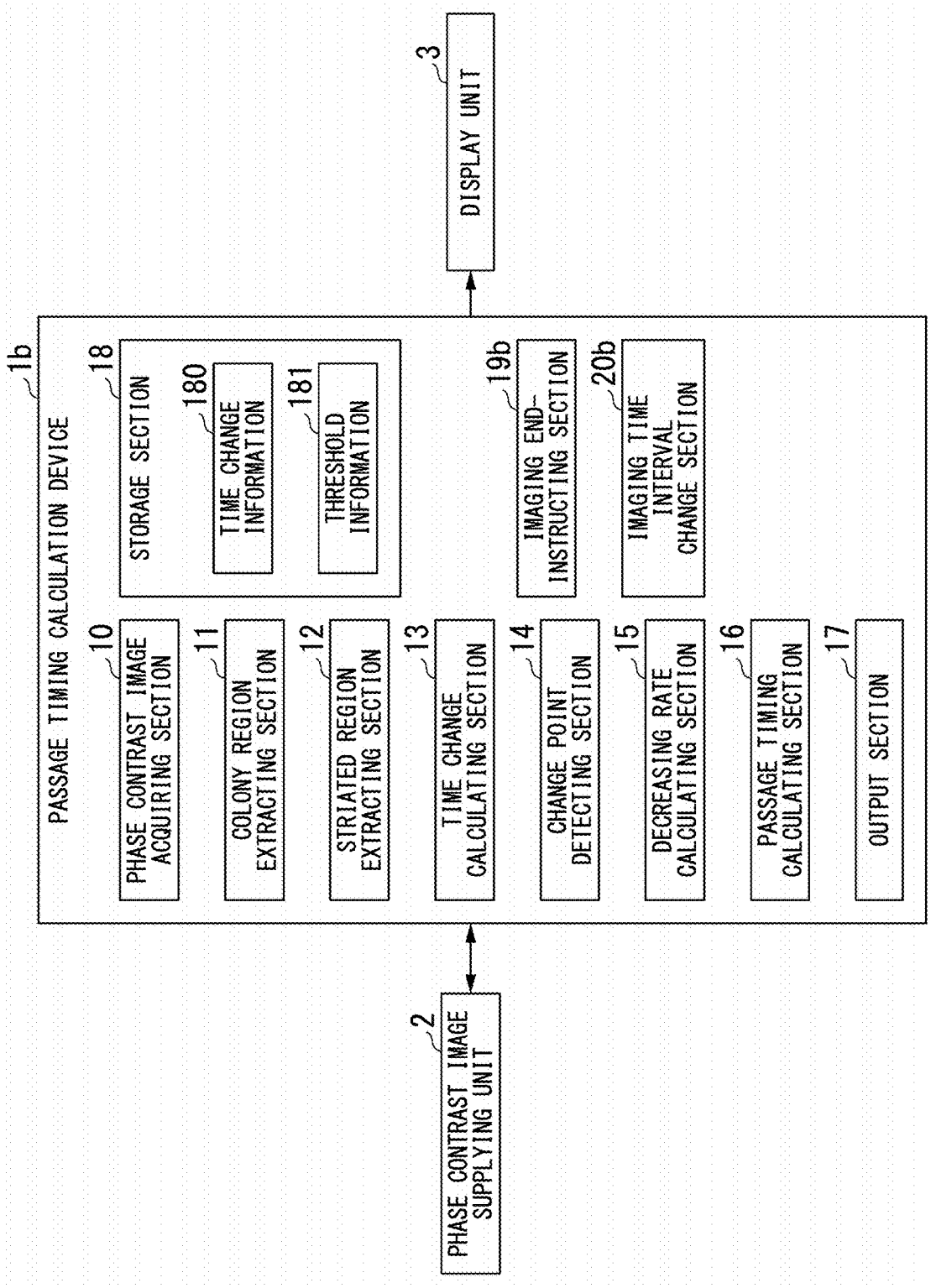
FIG. 8 is a diagram which shows an example of a configuration of a passage timing calculation device according to a third embodiment of the present invention.

FIG. 8 is a diagram which shows an example of a configuration of the passage timing calculation device 1b according to the present embodiment. If the passage timing calculation device 1b (FIG. 8) according to the present embodiment and the passage timing calculation device 1 (FIG. 2) according to the first embodiment are compared, these are different in the imaging end-instructing section 19b and the imaging time interval change section 20b. Here, the functions of other components (the phase contrast image acquiring section 10, the colony region extracting section 11, the striated region extracting section 12, the time change calculating section 13, the change point detecting section 14, the decreasing rate calculating section 15, the passage timing calculating section 16, and the output section 17) have the same as those in the first embodiment. The description of the same functions as those in the first embodiment will be omitted, and a portion different from the first embodiment will be mainly described in the third embodiment.

The imaging end-instructing section 19b supplies an end instruction indicating an end of imaging of pluripotent stem cells to the phase contrast image supplying unit 2 when the passage timing PT is calculated by the passage timing calculating section 16.

The imaging time interval change section 20b supplies an imaging time change instruction indicating that a time interval in which pluripotent stem cells are imaged is to be lengthened to the phase contrast image supplying unit 2 after the change point M1 is detected by the change point detecting section 14.

Next, processing in which the passage timing calculation device 1b calculates the passage timing PT will be described with reference to FIG. 9. The processing in which the passage timing calculation device 1b calculates the passage timing PT and the processing (FIG. 3) in which the passage timing calculation device 1 of the first embodiment calculates a passage timing are different in the passage timing calculation processing of step S160.

In the processing in which the passage timing calculation device 1b calculates the passage timing PT, the number of frames of the plurality of phase contrast images PS does not have to be determined in advance.

The passage timing calculation processing performed by the passage timing calculation device 1b will be described with reference to FIG. 9.

Figure 9:
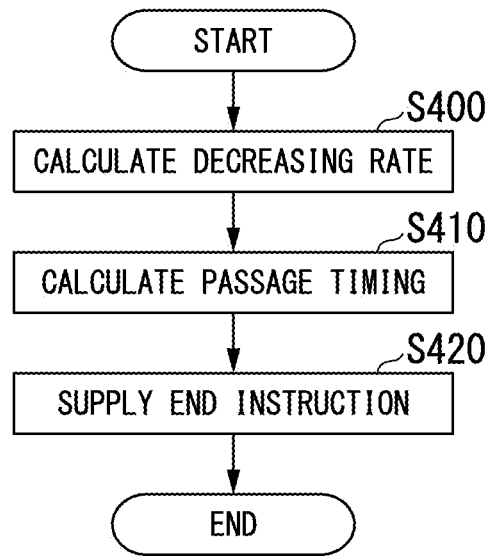
FIG. 9 is a diagram which shows a first example of passage timing calculation processing according to the third embodiment of the present invention.

FIG. 9 is a diagram which shows a first example of the passage timing calculation processing according to the present embodiment. Since processings of step S400 and step S410 are the same as the processings of step S200 and step S210 in FIG. 5, the description thereof will be omitted.

Step S420: The imaging end-instructing section 19b supplies an end instruction to the phase contrast image supplying unit 2. That is, the imaging end-instructing section 19b instructs for an end of imaging of pluripotent stem cells when the passage timing PT is calculated by the passage timing calculating section 16.

The phase contrast image supplying unit 2 ends timelapse imaging on the basis of an end instruction supplied from the imaging end-instructing section 19b.

Since the passage timing calculation device 1b can end the imaging of pluripotent stem cells when the passage timing PT is calculated, the amount of data of the plurality of phase contrast images PS can be reduced.

Next, another example of the passage timing calculation processing performed by the passage timing calculation device 1b will be described with reference to FIG. 10.

Figure 10:
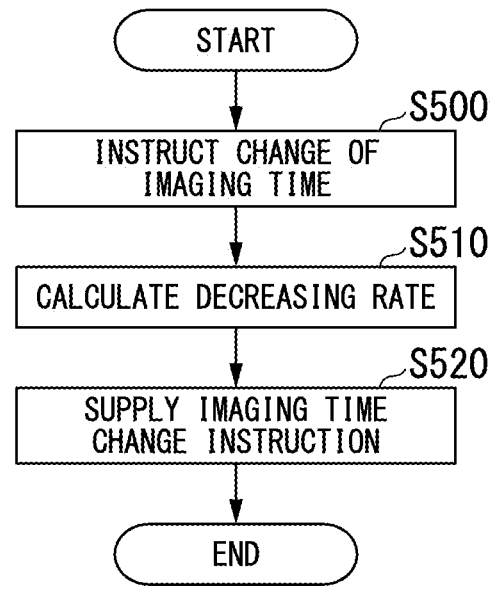
FIG. 10 is a diagram which shows a second example of the passage timing calculation processing according to the third embodiment of the present invention.

FIG. 10 is a diagram which shows a second example of the passage timing calculation processing according to the present embodiment. Since processings of step S510 and step S520 are the same as processings of step S200 and step S210 in FIG. 5, the description thereof will be omitted.

The change point detecting section 14 supplies information indicating that a change point has been detected in step S155 of FIG. 2 to the imaging time interval change section 20b before a start of the passage timing calculation processing of FIG. 10.

Step S500: The imaging time interval change section 20b supplies an imaging time change instruction to the contrast difference image supplying unit 2. That is, the imaging time interval change section 20b changes a time interval at which pluripotent stem cells are imaged after the change point M1 is detected by the change point detecting section 14.

The phase contrast image supplying unit 2 lengthens an imaging time interval of timelapse imaging from the length before the change on the basis of the imaging time change instruction supplied from the imaging time interval change section 20b.

The imaging time interval change section 20b may supply the imaging time change instruction to the phase contrast image supplying unit 2 after the passage timing PT is calculated by the passage timing calculating section 16. That is, the imaging time interval change section 20b may also change the time interval at which pluripotent stem cells are imaged after the passage timing PT is calculated by the passage timing calculating section 16.

The imaging time interval change section 20b may also shorten the interval of the imaging time of timelapse imaging from a length of the interval of the imaging time before the striated region ratio A calculated by the time change calculating section 13 is equal to or greater than a predetermined value when the striated region ratio A is equal to or greater than a predetermined ratio. Here, the predetermined ratio is, for example, zero. That is, the imaging time interval change section 20b shortens the length of the interval of the imaging time after the striated region SR has appeared if the striated region SR appears in the plurality of phase contrast images PS.

Since the time change G1 after the striated region SR has appeared is used to calculate the passage timing PT, the passage timing calculation device 1b can improve the accuracy in the calculation of the passage timing PT for the number N of frames of the plurality of phase contrast images PS by shortening the length of the interval of the imaging time after the striated region SR has appeared.

In addition, the imaging time interval change section 20b may also make the interval of the imaging time of timelapse imaging before the striated region ratio A calculated by the time change calculating section 13 is equal to or greater than the predetermined ratio longer than the length of a predetermined time.

Since the time change G1 after the striated region SR has appeared is used to calculate the passage timing PT, the passage timing calculation device 1b can reduce the amount of data of the plurality of phase contrast images PS before the striated region SR appears by making the interval of the imaging time for the time change G1 before the appearance of the striated region SR longer than the length of the predetermined time.

As described above, the passage timing calculation device 1b according to the present embodiment includes an imaging time interval change section 20b. The imaging time interval change section 20b changes the time interval at which pluripotent stem cells are imaged after the change point M1 is detected by the change point detecting section 14.

With this configuration, the passage timing calculation device 1b according to the present embodiment can lengthen the time interval at which pluripotent stem cells are imaged after the change point M1 is detected, so that it is possible to reduce the amount of data of the plurality of phase contrast images PS.

The present inventors have also found that colonies in which a striated region has appeared have a high probability of maturing thereafter, and colonies in which a striated region is not observed are highly likely not to be mature. Therefore, the passage timing calculation devices 1, 1a, and 1b in the embodiments described above may also have functions of determining that a culture has been cancelled and displaying a result of the determination on the display unit 3 when the striated region extracting section 12 does not extract a striated region within a predetermined period, or when the area of a striated region does not reach a predetermined area.

In addition, a part of the passage timing calculation devices 1, 1a, and 1b in the embodiments described above, for example, the phase contrast image acquiring section 10, the colony region extracting section 11, the striated region extracting section 12, the time change calculating section 13, the change point detecting section 14, the decreasing rate calculating section 15, the passage timing calculating sections 16 and 16a, the output section 17, the imaging end-instructing section 19b, and the imaging time interval change section 20b, may be realized using a computer. In this case, a program for realizing this control function may be recorded on a computer-readable recording medium, and the program recorded on the recording medium may be read and executed by a computer system. The "computer system" herein is a computer system embedded in the passage timing calculation devices 1, 1a, and 1b, and includes an OS and hardware such as peripheral devices. In addition, the "computer-readable recording medium" refers to a portable medium such as a flexible disk, a magneto-optical disc, a ROM, or a CD-ROM, or a storage device such as a hard disk embedded in a computer system. Furthermore, the "computer-readable recording medium" may include a device that dynamically holds a program for a short period of time, like a communication line when a program is transmitted via a network such as the Internet or a communication line such as a telephone line, and a device that holds the program for a certain period of time, like a volatile memory inside the computer system serving as a server or a client in this case. In addition, the program described above may be a program for realizing a part of the functions described above, and may also be furthermore a program for realizing the functions described above in combination with a program already recorded in the computer system.

In addition, a part or all of the passage timing calculation devices 1, 1a and 1b in the embodiments described above may be realized as an integrated circuit such as Large Scale Integration (LSI). Each functional block of passage timing calculation devices 1, 1a, and 1b may be made into a processor individually, or a part or all of them may be integrated into a processor. Moreover, a method of making an integrated circuit is not limited to the LSI, and may be realized by a dedicated circuit or a general-purpose processor. Furthermore, when a technology of making an integrated circuit that replaces the LSI appears due to advances in a semiconductor technology, an integrated circuit based on this technology may also be used.

Although one embodiment of the present invention has been described in detail with reference to the drawings, the specific configuration is not limited to the description above, and various design changes and the like can be made within a range not departing from the gist of the present invention.

REFERENCE SIGNS LIST 1, 1a, 1b Passage timing calculation device
2 Phase contrast image supplying unit
3 Display unit
10 Phase contrast image acquiring section
11 Colony region extracting section
12 Striated region extracting section
13 Time change calculating section
14 Change point detecting section
15 Decreasing rate calculating section
16, 16a Passage timing calculating section
17 Output section
18, 18a Storage section
180 Time change information
181 Threshold information
181a passage timing information
19b Imaging end-instructing section
20b Imaging time interval change section

The invention claimed is:
1. A passage timing calculation device comprising:
a processor;
a memory encoded with instructions executed by the processor, the instructions causing the processor to perform operations comprising:
extracting a colony region of pluripotent stem cells from a plurality of images of pluripotent stem cells captured over time in a process of culturing the pluripotent stem cells;
extracting, as an extraction target region, a high-contrast region in which contrast in a gap between the plurality of pluripotent stem cells becomes higher during a transition state between a colony immature state and a mature state, the high-contrast region being a region in which a striated pattern is present in the plurality of images due to the higher contrast;
calculating a time change in a ratio of an area occupied by the extraction target region to a colony region from the plurality of images of pluripotent stem cells captured over time; and
calculating a passage timing of the pluripotent stem cells based on the time change.
2. The passage timing calculation device according to claim 1, wherein the instructions cause the processor to execute operations further comprising:
calculating a decreasing rate of the ratio after the change point with respect to the calculated time change, and
calculating the passage timing based on the calculated decreasing rate and a predetermined threshold value.
3. The passage timing calculation device according to claim 2, wherein the instructions cause the processor to execute operations further comprising:
changing the predetermined threshold value.
4. The passage timing calculation device according to claim 1, wherein the instructions cause the processor to execute operations further comprising:
determining the passage timing based on the time change and passage timing information in which the time change and the passage timing are associated with each type of the pluripotent stem cells in advance.
5. The passage timing calculation device according to claim 1, wherein the instructions cause the processor to execute operations further comprising:
changing a time interval at which the pluripotent stem cells are imaged.
6. The passage timing calculation device according to claim 5, wherein the instructions cause the processor to execute operations further comprising:
shortening the time interval when the ratio in which the time change calculated is equal to or greater than a predetermined ratio.
7. The passage timing calculation device according to claim 5, wherein the instructions cause the processor to execute operations further comprising:

lengthening the time interval when the ratio in which the time change calculated is equal to or greater than a predetermined ratio.

8. The passage timing calculation device according to claim 1, wherein the instructions cause the processor to execute operations further comprising:

extracting the extraction target region by excluding an abnormal region in the colony region wherein the abnormal region is a region which does not have a portion whose brightness is higher than a predetermined value in surroundings of the region.

9. The passage timing calculation device according to claim 1, wherein the instructions cause the processor to execute operations further comprising:

acquiring a plurality of phase contrast images as the plurality of the images.

10. The passage timing calculation device according to claim 1, wherein the instructions cause the processor to execute operations further comprising:

outputting the passage timing.

11. The passage timing calculation device according to claim 10, wherein the instructions cause the processor to execute operations further comprising:

displaying the calculated passage timing.

12. The passage timing calculation device according to claim 10, wherein the instructions cause the processor to execute operations further comprising:

determining that a culture has been cancelled when the extraction target region is not extracted within a predetermined period, or when the area of the extraction target region does not reach a predetermined area; and displaying a result of the determination.

13. A system configured from an image processing device that includes an image acquisition section configured to image pluripotent stem cells over time in a process of culturing the pluripotent stem cells and acquire a plurality of images, and the passage timing calculation device according to claim 10.

14. A passage timing calculation method comprising:

extracting a colony region of pluripotent stem cells from a plurality of images of pluripotent stem cells captured over time in a process of culturing the pluripotent stem cells;

extracting, as an extraction target region, a high-contrast region in which contrast in a gap between the plurality of pluripotent stem cells becomes higher during a transition state between a colony immature state and a mature state, the high-contrast region being a region in which a striated pattern is present in the plurality of images due to the higher contrast;

calculating a time change in a ratio of an area occupied by the extraction target region to a colony region from the plurality of images of pluripotent stem cells captured over time; and calculating a passage timing of the pluripotent stem cells based on the time change.

15. A non-transitory computer-readable recording medium for recording a program for causing a computer to execute operations comprising:

extracting a colony region of pluripotent stem cells from a plurality of images of pluripotent stem cells captured over time in a process of culturing the pluripotent stem cells;

extracting, as an extraction target region, a high-contrast region in which contrast in a gap between the plurality of pluripotent stem cells becomes higher during a transition state between a colony immature state and a mature state, the high-contrast region being a region in which a striated pattern is present in the plurality of images due to the higher contrast;

calculating a time change in a ratio of an area occupied by the extraction target region to a colony region from the plurality of images of pluripotent stem cells captured over time; and calculating a passage timing of the pluripotent stem cells based on the time change.

* * * * *